United States Patent [19]

Siposs

[11] Patent Number: 4,725,266
[45] Date of Patent: * Feb. 16, 1988

[54] LEFT VENTRICLE VACUUM CONTROL AND PRESSURE RELIEF VALVE

[76] Inventor: George G. Siposs, 2855 Velasco La., Costa Mesa, Calif. 92626

[*] Notice: The portion of the term of this patent subsequent to Feb. 10, 2004 has been disclaimed.

[21] Appl. No.: 884,190

[22] Filed: Jul. 10, 1986

Related U.S. Application Data

[63] Continuation-in-part of Ser. No. 715,928, Mar. 25, 1985, Pat. No. 4,642,097.

[51] Int. Cl.[4] .......................................... F16K 17/164
[52] U.S. Cl. .................................... 604/119; 604/118; 604/129; 604/247; 137/512.3
[58] Field of Search ................ 604/9, 34, 35, 118, 604/119, 128, 129, 236, 237, 247; 137/853, 512.3

[56] References Cited

U.S. PATENT DOCUMENTS

| | | | |
|---|---|---|---|
| 3,384,113 | 5/1968 | Pennisi | 137/853 |
| 3,416,567 | 12/1968 | Von Dardel et al. | 604/34 |
| 3,995,617 | 12/1976 | Watkins et al. | 128/1 D |
| 4,502,502 | 3/1985 | Krug | 604/118 |
| 4,642,097 | 2/1987 | Siposs | 604/119 |
| 4,657,536 | 4/1987 | Dorman | 604/9 |
| 4,671,786 | 6/1987 | Krug | 604/118 |

Primary Examiner—Stephen C. Pellegrino
Assistant Examiner—Ralph Lewis
Attorney, Agent, or Firm—Allen A. Dicke, Jr.

[57] ABSTRACT

The valve is positioned in the left ventricle drain line and includes a check valve which permits flow only away from the heart and downstream of the check valve includes a vent valve which prevents buildup of pressure. In addition, the valve includes a vacuum orifice to limit left ventricle drain line vacuum intensity applied to the heart.

8 Claims, 4 Drawing Figures

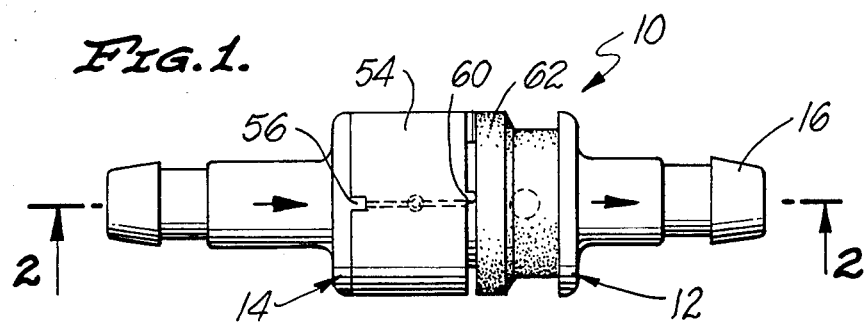
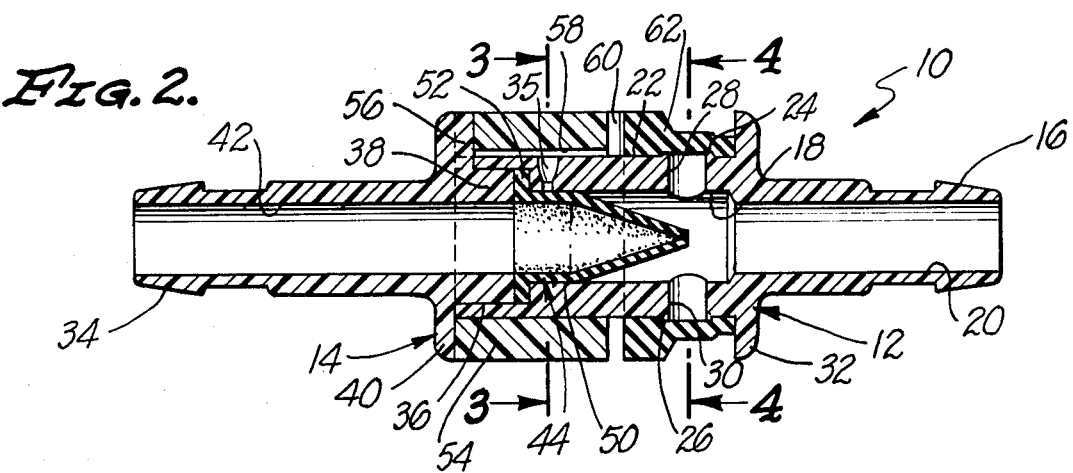
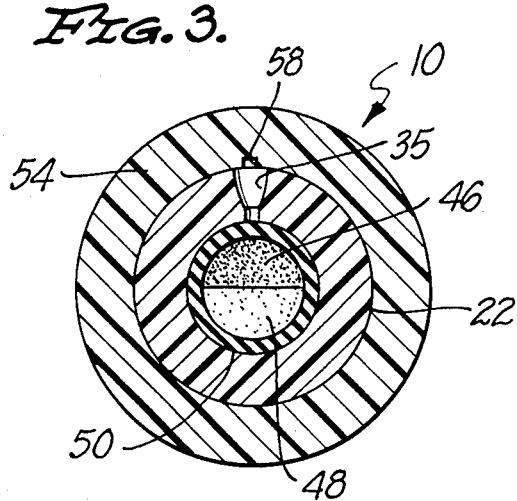
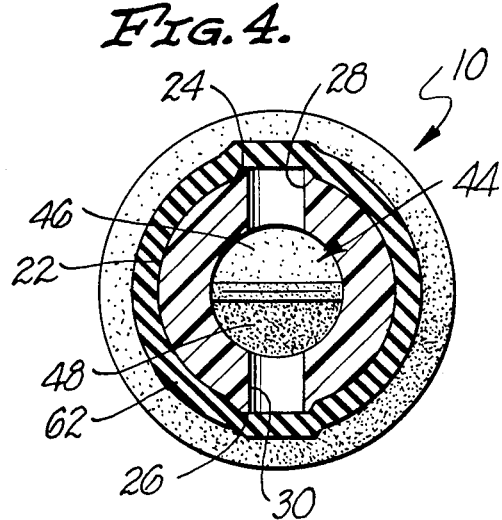

LEFT VENTRICLE VACUUM CONTROL AND PRESSURE RELIEF VALVE

CROSS REFERENCE

This application is a continuation-in-part of patent application Ser. No. 715,928, filed Mar. 25, 1985 for "LEFT VENTRICLE VACUUM CONTROL AND PRESSURE RELIEF VALVE," now U.S. Pat. No. 4,642,097.

BACKGROUND OF THE INVENTION

This invention is directed to a valve which limits the vacuum applied to the left ventricle during open-heart operation, prevents reverse flow to the heart, and vents the downstream line of gas or blood should pressure rise above atmosphere.

During some open-heart procedures, even though the heart is bypassed with the open-heart tubing, some blood finds its way into the left ventricle of the heart. Unless the blood is drained from the left ventricle, the blood causes the heart to distend. Such distension makes it difficult or impossible to resuscitate the heart at the end of the procedure. For this reason, some surgeons attach a slender tubing to the left ventricle to drain the blood from it. A suction pump may be used to provide the vacuum to remove the blood. Several problems may be caused by such a method. One problem arises if the opening of the drain line tube attaches itself to the inside of the heart chamber. This causes suction to be stopped, and the tubing must be wrenched away from the tissue. This causes trauma to the chamber tissue. The present valve limits the suction intensity to a reasonable level so that it is easier to pull the tube away from tissue.

Another problem which may occur during left heart venting arises from the fact that the amount of suction to the heart through the left ventricle drain line is regulated by the speed of the vacuum pump. The vacuum pump is controlled by the heart-lung machine technician who is not close to the surgical field, so the amount of suction intensity must be limited to prevent collapse of the tubing or tissue trauma when the distal end of the line is occluded.

Another problem which may occur is the buildup of pressure in the left ventricle drain line. This would drive air into the heart and cause an air embolism and even possible death of the patient. Such inadvertent pressure in the left ventricle drain line could be caused by any one of several means. For example, the vacuum pump switch could accidentally be positioned to run the pump in reverse so that, instead of suction, pressure would be produced in the drain line. Another possible cause of such pressure would occur when the suction pump is connected to discharge into a closed reservoir in which the pump causes a pressure buildup. In such a case, there is a chance that when the pump is stopped, the pressure may leak back through the drain line into the heart. Another cause of pressure buildup in the drain line is in the structure of the roller pump. In a roller pump, the tubing may be accidentally inserted in a backward orientation into the pump housing so that, even if the pump switch is in the "Forward" position, the pump is working backward.

In order to prevent such problems from causing dangers to the patient, the present left ventricle vacuum control and pressure relief valve was created. This valve prevents flow toward the heart and allows flow only away from the heart, whether the flow be blood or air. A vacuum vent orifice in the valve body is covered on the interior by a resilient sleeve so that the vacuum drawn downstream of the check valve is limited. Furthermore, the valve of this invention permits any above atmospheric pressure in the downstream line to be vented to the atmosphere instead of being transmitted to the heart. When the venting is accompanied by the escape of blood from the valve, the surgeon is immediately notified that something is wrong (for example, there is inadequate suction to remove the blood) and can take corrective measures.

SUMMARY OF THE INVENTION

In order to aid in the understanding of this invention, it can be stated in essentially summary form that it is directed to a left ventricle vacuum limit and pressure relief valve which includes a body having a passage therethrough and a check valve therein which permits flow only from the inlet toward the outlet. Downstream of the check valve is a pressure vent valve and vacuum vent valve downstream of the check valve which allows air to bleed into the passage when vacuum is applied.

It is, thus, an object and advantage of this invention to provide a valve for the left ventricle drain line which permits flow only away from the heart.

It is another purpose and advantage of this invention to provide a valve for the left ventricle drain line which does not allow full vacuum to be applied to the heart.

It is a further object and advantage of this invention to provide a valve for the left ventricle drain line which automatically vents pressure in excess of atmospheric pressure to prevent pressure buildup toward the heart, and to vent air if pressure builds up in the outlet end of the drain line.

It is a further object and advantage of this invention to provide a valve for the left ventricle drain line which is simple, small, and can be accurately massproduced and pre-sterilized so that it can be easily and safely inserted in the left ventricle drain.

Other objects and advantages of this invention will become apparent from a study of the following portion of this specification, the claims and the attached drawings.

BRIEF DESCRIPTION OF THE DRAWINGS

FIG. 1 is a side-elevational view of the valve in accordance with this invention.

FIG. 2 is an enlarged section taken generally along the line 2—2 of FIG. 1.

FIG. 3 is an enlarged transverse section taken generally along the line 3—3 of FIG. 2.

FIG. 4 is an enlarged section taken generally along the line 4—4 of FIG. 2.

DESCRIPTION OF THE PREFERRED EMBODIMENT

The left ventricle vacuum limit and pressure relief valve of this invention is generally indicated at 10 in FIGS. 1, 2, 3 and 4. Valve 10 is shown in longitudinal section in FIG. 2 and is shown in transverse section in FIGS. 3 and 4. Valve 10 has a body 12 and an inlet fitting 14. Body 12 has an outlet barbed nipple 16 on its outlet end with the nipple sized to be received in the left ventricle drain line. Passage 18 in the body adjoins passage 20 in the nipple, with the passages extending end-to-end through the body, defining a central axis therethrough.

Body 12 has an external surface 22 which is cylindrical about the axis, except for nipples 24 and 26 respectively at the outlet ends of pressure relief passages 28 and 30. Shoulder 32 extends radially outward at the right end of the body. Relief passages 28 and 30 are radial passages of circular cross section which extend from the internal passage 18 to the external surface 22. Vacuum vent orifice 35 also is a radially oriented passage of circular cross section extending from the internal passage 18 to the external surface 22.

Cap 14 has a barbed inlet nipple 34 thereon sized the same as nipple 16 so that the left ventricle drain line can be cut at an appropriate location and the valve 10 inserted therein, with the valve connected to both ends of the line. Body 12 has a circular flange 36 extending to the left therefrom, as seen in FIG. 2, which embraces around a rightward extending circular extension 38 of the cap 14. These interengaging portions provide alignment for the cap on the body and provide for securement of the cap on the body, as by adhesive means, heat sealing, or preferably by ultrasonic joining. Cap 14 has shoulder 40 thereon which corresponds to shoulder 32.

Inlet nipple 34 and cap 14 also have passage 42 therein which is in alignment with passages 18 and 20. Duckbill valve 44 is structured so that it permits flow from left to right through valve 10, as seen in FIG. 2, in the inlet nipple 34 and out of outlet nipple 16. The valve 44 is an elastomeric molding of generally cylindrical configuration, but, as seen in FIG. 3, has a pair of flat lips 46 and 48 which lie together. These are conventionally molded in one piece and slit afterwards. The result is a valve which opens to flow in the left-to-right direction with very low differential pressure and lies closed essentially without a differential pressure. If the pressure is higher on the right side, as seen in FIG. 2, the valve lips are forced closed to inhibit flow. Such valves are often called "duckbill" valves from their physical resemblance. Thus, valve 44 is a check valve which permits flow only in the left-to-right direction through valve 10. Passage 42 aligns with the interior opening within valve 44, while passage 18 embraces the main body 50 of valve 44. An outwardly directed flange 52 is captured between the body 12 and extension 38 on cap 14.

The cylindrical body 50 of duckbill valve 44 lies across the interior opening of vacuum vent orifice 35 where it enters into passage 18. When the interior pressure is higher than the exterior pressure, the body 50 closes the vacuum vent orifice. When the interior pressure within passage 18 is lower than the exterior atmospheric pressure, the pressure differential working through the area of vacuum vent orifice 35 onto the exterior of body 50 tend to displace the body to permit the entry of the atmospheric air. The size of the vacuum vent 35 where it intersects with passage 18 and the strength of body 50 determine the pressure differential at which atmospheric air will be permitted to enter into passage 18. Vacuum vent orifice 35 preferably has a diameter of about 0.020 inch to 0.030 inch, which is a conventional vent opening size. As seen in FIGS. 2 and 3, the shape of vacuum vent orifice 35 carefully controls the size of the vent orifice where it intersects with passage 18. In this way, the lower limit of pressure downstream of the check valve 44 is controlled. It is to be noted that the entry of air is downstream of the check valve so that it is isolated from the left ventricle.

Collar 54 surrounds surface 22 and lies against shoulder 40. Key 56 on shoulder 40 engages in the corresponding keyway in collar 54 to prevent rotation of the collar. Slot 58, see FIGS. 2 and 3, overlies vacuum vent 35 when the key is engaged in its keyway. In this way, the exterior opening of vent 35 is protected. Nib 60 is formed on collar 54 to allow easy egress of air.

Elastic ring 62 is engaged around external surface 22 and lies against shoulder 32. Elastic ring 62 is a cylindrical tube which gently engages upon surface 22 and on nipples 24 and 26. When the pressure rises in the central chamber of valve 10, in passage 18, the pressure in relief passages 28 and 30 lifts elastic ring 62 to permit venting of the pressure. However, when there is vacuum in passage 18, elastic ring 62 overlies the opening of relief passages 28 and 30 to prvent inflow from atmosphere. Thus, elastic ring 62 serves as a one-way valve and as the active member in the pressure relief function of valve 10. Nib 62 engages against elastic ring 62 to hold the collar 54 in the leftward position illustrated in FIGS. 1 and 2.

As an economic and satisfactory method of manufacture, the body 12, cap 14 and sleeve 54 can be injection-molded of fairly rigid thermoplastic synthetic polymer composition bicompatible material such as polycarbonate or ABS. Almost all surfaces of the valve are surfaces of revolution about the axial centerline through the valve. This design reduces molding costs so as to provide an economic valve. Valve 48 is injection-molded of an elastomer, and after the molding, the valve opening is cut with a razor or the like. Elastic ring 62 can be sliced from an extruded tube or can be molded from thermoplastic elastomer. As illustrated, the elastic ring 62 is of two external diameters and thus must be molded. The smaller diameter over the nipples 24 and 26 is to permit a lighter elastic force of the ring onto the closure of the pressure relief passages. The level of pressure relief can be controlled by the diameter, hardness, and thickness of the ring. After the assembly of the parts into the organization shown in FIG. 2, the structure is permanently assembled by attachment between flange 36 and extension 38, by adhesive means or ultrasonic bonding, for example. All of the parts must be of suitable characteristics for sterilization.

In the preferred utilization, the valve 10 is placed in the left ventricle vent line about 2 feet from and level with the heart so that the valve is positioned near the patient's groin on the sterile drape so that it may be observed by the surgeon. Alternatively, the valve can be placed in the line closer to the perfusionist's pump. The amount of suction desired in most cases is about 150 mm Hg. The pump speed is adjusted so that this level of vacuum is reached. Should the suction pump not be operating or should the suction pump be operating too slowly and the heart is putting blood into the left ventricle drain line, blood in the valve will leak out of the valve through relief passages 28 and 30. This presence of blood will immediately warn the surgical team of an undesirable condition. Efforts can be made to increase suction to withdraw the blood from the left ventricle drain line. In this manner, the blood is safely drained from the left ventricle, with the level of vacuum being limited by vent 35 to a proper level. The valve incorporates structure which permits the relief of pressure and incorporates structure which prevents the reverse flow of fluid through the left ventricle drain line and, accordingly, the requirements of the application are satisfied.

This invention has been described in its presently contemplated best mode, and it is clear that it is susceptible to numerous modifications, modes and embodiments within the ability of those skilled in the art and without the exercise of the inventive faculty. Accordingly, the scope of this invention is defined by the scope of the following claims.

What is claimed is:

1. A valve for the control of vacuum in a physiological liquid drain line, said valve comprising:
   a valve body connectible in the drain line between a patient and a suction pump, said body having a flow passage therethrough having an inlet end and an outlet end, a vacuum vent passage in said body extending from said flow passage through said body to the atmosphere, a check valve in said flow passage within said body for limiting flow through said flow passage through said body from said inlet end of said body to said outlet end of said body, said check valve being a duckbill valve made of elastomeric material and having a resilient valve body within said flow passage covering the interior of said vacuum vent passage to limit the vacuum in said flow passage;
   walls defining a pressure relief passage in said body extending from said flow passage to the exterior of said body; and
   a tubular elastomeric member on said body covering said pressure relief passage so that when pressure in said flow passage is below atmospheric pressure said pressure relief passage is closed and when pressure in said flow passage is above atmospheric pressure, fluid in said flow passage discharges out of said pressure relief passage out from under said tubular elastomeric member.

2. The valve of claim 1 further including a check valve in said flow passage within said body for allowing flow through said flow passage through said body from said inlet end of said body to said outlet end of said body.

3. The valve of claim 2 wherein said vacuum vent passage is positioned between said check valve and said outlet end of said body.

4. A valve comprising:
   a valve body, an inlet connection and an outlet connection on said valve body for connection in a drain line between a patient and a suction pump, a passage through said valve body from said inlet to said outlet;
   a generally radially oriented single vacuum vent passage of generally circular cross section in said valve body from said through passage to the exterior of said body;
   an elastomeric check valve within said valve body having a portion thereof lying against the interior of said vacuum vent passage in said body so that when the pressure within said through passage falls below a predetermined value air flows in through said vacuum vent passage to limit the degree of vacuum within said through passage;
   walls defining a relief passage in said valve body extending from said through passage to the exterior of said body; and
   an elastomeric member on said body covering said relief passage so that when pressure in said through passage is below external pressure said relief passage is closed and when pressure in said through passage is above external pressure, fluid in said through passage discharges out of said relief passage out from under said elastomeric member.

5. The valve of claim 4 wherein said check valve is a duckbill valve.

6. A valve comprising:
   a valve body, an inlet connection and an outlet connection on said valve body for connection in a drain line between a patient and a suction pump, a flow passage through said valve body from said inlet connection to said outlet connection, said valve body having a substantially cylindrical external surface thereon;
   a vacuum vent passage in said body from said flow passage to the external surface of said body;
   a resilient tube positioned within said flow passage and lying against the interior surface of said flow passage and covering said vacuum vent passage where it enters the flow passage through said body, said resilient tube being of such resilience and said vacuum vent pasasge being of such size as to permit venting of atmospheric air inward into said valve body through said vacuum vent passage;
   a relief pasasge in said body from said flow pasasge to the exterior of said body through the substantially cylindrical external surface of said body;
   an elastomeric member on the exterior of said body, said elastomeric member overlying said relief passage in said body so that said elastomeric member acts to vent pressure from the flow passage through said body to the exterior of said body when the pressure in said flow passage exceeds a predetermined value; and
   a check valve in said flow passage within said body to limit flow through said flow passage through said body from said inlet to said outlet.

7. The valve of claim 6 wherein said vacuum vent passage is positioned between said check valve and said outlet.

8. The valve of claim 6 wherein said check valve is formed as part of said resilient tube positioned within said flow passage which lies against the interior surface of said flow passage and covers said vacuum vent passage.

* * * * *